(12) United States Patent
Huang et al.

(10) Patent No.: US 12,429,407 B1
(45) Date of Patent: Sep. 30, 2025

(54) THERMAL-HYDROLOGICAL-MECHANICAL-CHEMICAL COUPLING EXPLOITATION EXPERIMENTAL DEVICE OF DEEP OIL AND GAS RESERVOIR AND SIMULATION SYSTEM

(71) Applicant: China University of Petroleum (East China), Dongying (CN)

(72) Inventors: Zhaoqin Huang, Dongying (CN); Xu Zhou, Dongying (CN); Jun Yao, Dongying (CN); Lei Yang, Dongying (CN); Heng Zhou, Dongying (CN); Xu Zhang, Dongying (CN); Yufan He, Dongying (CN); Feng Sun, Dongying (CN); Xiaoguang Huang, Dongying (CN); Liang Gong, Dongying (CN); Hai Sun, Dongying (CN)

(73) Assignee: China University of Petroleum (East China), Dongying (CN)

( * ) Notice: Subject to any disclaimer, the term of this patent is extended or adjusted under 35 U.S.C. 154(b) by 0 days.

(21) Appl. No.: 18/964,278

(22) Filed: Nov. 29, 2024

(30) Foreign Application Priority Data

Jun. 5, 2024 (CN) .......................... 202410718995.9

(51) Int. Cl.
*G01N 3/18* (2006.01)
*G01N 3/12* (2006.01)
*G01N 33/24* (2006.01)

(52) U.S. Cl.
CPC ................. *G01N 3/18* (2013.01); *G01N 3/12* (2013.01); *G01N 33/24* (2013.01); *G01N 2203/0048* (2013.01)

(58) Field of Classification Search
CPC ............ G01N 3/18; G01N 3/12; G01N 33/24; G01N 2203/0048; G01N 1/286; G01N 3/24; G01N 3/02; G01N 15/082; G01N 3/04; G01N 3/00; G01N 1/08; G01N 3/22;
(Continued)

(56) References Cited

U.S. PATENT DOCUMENTS

2019/0204288 A1* 7/2019 Zhang ..................... G01N 3/10

FOREIGN PATENT DOCUMENTS

CN  114486996  *  5/2022  ............. G01N 25/16

* cited by examiner

*Primary Examiner* — Brandi N Hopkins
(74) *Attorney, Agent, or Firm* — KPPB Law; Kermit D. Lopez; Luis M. Ortiz (57) ABSTRACT

Provided are a thermal-hydrological-mechanical-chemical coupling exploitation experimental device for a deep oil and gas reservoir, and a simulation system. The device includes a loading bin, a sample holding bin, a true triaxial pressure loading mechanism arranged on the loading bin, a temperature control system arranged on the true triaxial pressure loading mechanism, and a monitoring system having a detection element arranged in the rock sample and the sample holding bin. A sample entry port is formed in one side surface of the loading bin. The sample holding bin has one end slidably arranged in the sample entry port, can be sealed and connected with the sample entry port, and is configured for placing and fixing a rock sample. Multiple through holes are uniformly formed on an outer end cover of the sample holding bin and are configured for detecting and adding water, gas, and oil.

12 Claims, 3 Drawing Sheets

(58) Field of Classification Search
CPC ...... G01N 15/0806; G01N 3/56; B23D 15/06; B23D 15/04
USPC .................................................. 73/818, 801
See application file for complete search history.

THERMAL-HYDROLOGICAL-MECHANICAL-CHEMICAL COUPLING EXPLOITATION EXPERIMENTAL DEVICE OF DEEP OIL AND GAS RESERVOIR AND SIMULATION SYSTEM

CROSS-REFERENCE TO RELATED APPLICATION

This patent application claims the benefit and priority of Chinese Patent Application No. 202410718995.9 filed with the China National Intellectual Property Administration on Jun. 5, 2024, the disclosure of which is incorporated by reference herein in its entirety as part of the present application.

TECHNICAL FIELD

The present disclosure relates to the technical field of physical experiments of oil and gas reservoirs, and in particular to a thermal-hydrological-mechanical-chemical coupling exploitation experimental device for a deep oil and gas reservoir and a simulation system.

BACKGROUND

In recent years, with the development of global oil and gas exploitation, oil and gas exploitation has gradually entered three major exploitation fields: onshore deep oil and gas, offshore deep-water oil and gas, and unconventional oil and gas. The deep oil and gas exploitation in China has also made a breakthrough, and various ultra-deep oil and gas reservoirs have been discovered in Tarim Basin. The exploitation of deep oil and gas reservoirs will become an important strategic direction for increasing oil and gas storage and production in China, which will be also a realistic field and an inevitable trend to achieve energy breakthrough in China.

At present, most of the existing researches on mechanical properties, constitutive relations and seepage experiments of the rock are based on conventional simulation devices, and there are few physical experiment researches considering the influence of many factors such as deep high-temperature, high-pressure and high-stress thermal-hydrological-mechanical coupling, so it is necessary to carry out physical experiments under high temperature, high pressure and high stress conditions to investigate mechanical properties and constitutive relations of the rock. Under the thermal-hydrological-mechanical coupling effect, the exploitation mechanism of exploitation modes with different well patterns, different injection methods and injection media, and pressure and acidification techniques for various well types remain unclear. Therefore, it is necessary to carry out physical experiments in a high-temperature and high-pressure in-situ environment. Under the thermal-hydrological-mechanical coupling effect, the impact of deep high stress and temperature on oil and gas production and thermal energy exploitation is not well understood, highlighting the need for parameter sensitivity analysis and optimized experiments in the high-temperature and high-pressure in-situ environment. The theoretical and experimental results about compressive strength and deformation characteristics of deep rocks are limited. Therefore, it is necessary to carry out physical experiments on porosity and permeability sensitivity analysis in the high-temperature and high-pressure in-situ environment. Furthermore, under the thermal-hydrological-mechanical coupling effect, the saturation distribution and pressure variation in deep oil and gas reservoirs under high stress and temperature are unclear and need to be explored through dedicated physical experiments. Under the thermal-hydrological-mechanical coupling effect, the propagation mechanism of the fracture artificially fractured in the complex environment of deep oil and gas reservoirs is also unclear, Thus related physical experiments in high-temperature, high-pressure, and high-stress environments are required to elucidate fracture propagation laws across multiple physical fields and understand the influence of varying pressure conditions on fracture propagation. The existing Biot hydrological-mechanical coupling theory is based on small-deformation assumption, which cannot accurately describe the influence of rock interaction in deep oil and gas reservoir fluids. Therefore, it is vital to reveal the influence of thermal-hydrological-mechanical coupling mechanism on the rock interaction in the deep oil and gas reservoirs in the high-temperature, high-pressure and high-stress environment, and establish the nonlinear seepage law of fluid flow in the deep oil and gas reservoirs. Moreover the properties of the deep oil and gas reservoir are affected by high temperature, high pressure, and high stress. The traditional quasi-triaxial experimental platform cannot accurately restore the in-situ stress state of deep formation, and the true triaxial experimental platform cannot meet the in-situ environmental requirements of high temperature, high pressure and high stress, at the same time, and the small and medium-sized samples cannot truly represent the structural characteristics of the rock mass. Consequently, there is an urgent need to develop and establish a thermal-hydrological-mechanical-chemical coupling physical simulation experimental platform for an ultra-deep oil and gas reservoir and a deep oil and gas reservoir.

SUMMARY

An objective of the present disclosure is to provide a thermal-hydrological-mechanical-chemical coupling exploitation experimental device for a deep oil and gas reservoir and a simulation system to address the issues present in the existing technology, such that the thermal-hydrological-mechanical coupling experiment of the rock mass can truly reflect the structure characteristics of the rock mass.

To achieve above objectives the present disclosure employs the following technical solution:

The present disclosure provides a thermal-hydrological-mechanical-chemical coupling exploitation experimental device for a deep oil and gas reservoir, including a loading bin, a sample holding bin, a true triaxial pressure loading mechanism, a temperature control system, and a monitoring system. A sample entry port is formed in one side surface of the loading bin, the sample holding bin is able to be sealed and connected with the sample entry port, and is configured for placing and fixing a rock sample; multiple through holes communicating with the sample holding bin are uniformly formed on an outer end cover of the sample holding bin, and a sealing member is arranged on the plurality of through holes; the plurality of through holes are configured for detecting and injecting water, gas and oil; the true triaxial pressure loading mechanism is arranged on the loading bin; the temperature control system is arranged on the true triaxial pressure loading mechanism, and a detection element of the monitoring system is arranged in the rock sample and the sample holding bin.

In some embodiments, the true triaxial pressure loading mechanism includes an X-axis servo loading system, a Y-axis flexible loading system, and a Z-axis servo loading system; the X-axis servo loading system and the Z-axis servo loading system are symmetrically arranged on respective side surfaces of the loading bin; and the Y-axis flexible loading system is configured to load confining pressure on the rock sample through the plurality of through holes.

In some embodiments, each of the X-axis servo loading system and the Z-axis servo loading system is a multi-stage arrayed hydraulic cylinder, a servo loading pump is connected to the multi-stage arrayed hydraulic cylinder, and a displacement sensor and a load sensor are arranged on the multi-stage arrayed hydraulic cylinder.

In some embodiments, multiple sealing blocks are fixedly arranged at a top and bottom of the sample holding bin, an insertion hole is formed in each sealing block, a bearing column is slidably arranged in the insertion hole, a bearing plate is connected to an upper bearing column, and a support seat is connected to a lower bearing column and is configured for fixing the rock sample; T-shaped bearing columns are configured to be arranged on both sides of the rock sample, and the bearing columns are used to connect with the X-axis servo loading system and the Z-axis servo loading system.

In some embodiments, the temperature control system is arranged on the Y-axis flexible loading system, and includes a temperature sensor, a heating system, and a refrigeration system. Both the heating system and the refrigeration system are arranged on the circulation pipeline of the Y-axis flexible loading system.

In some embodiments, the monitoring system includes an acoustic emission sensor, a pressure sensor, a temperature sensor located within the loading bin, and a resistive probe positioned within the rock sample.

In some embodiments, an outer end of the sample holding bin is provided with a sealing ring for sealing the sample entry port, and the sealing member is a ferrule-type joint; and a heat shrinkable tube is configured for sealing the rock sample and is made of tetrafluoroethylene resin.

In some embodiments, a support plate is connected to the outer end cover of the sample holding bin by a bolt, a pair of telescopic rods and a pair of guide columns are arranged on four corners of the support plate respectively, the telescopic rods and the guide columns each are arranged diagonally, and multiple rollers are arranged on a bottom of the support plate and are configured for rolling on a support platform.

The present disclosure further provides a thermal-hydrological-mechanical-chemical coupling simulation system for the deep oil and gas reservoir, which includes the aforementioned thermal-hydrological-mechanical-chemical coupling exploitation experimental device for the deep oil and gas reservoir, a seepage system, and a data collection and analysis system, wherein the seepage system includes a constant speed and constant pressure pump, volumetric containers, and a well network system; the well pattern system is configured to be arranged on the rock sample in the thermal-hydrological-mechanical-chemical coupling exploitation experimental device for the deep oil and gas reservoir; water, gas and oil are connected to respective volumetric containers through respective constant-speed and constant-pressure pumps; the volumetric containers communicate with the well pattern system; and the thermal-hydrological-mechanical-chemical coupling exploitation experimental device for the deep oil and gas reservoir is able to carry out two-rigid and one-flexible type triaxial pressure loading on the rock sample; the data collection and analysis system includes a data collection unit and a computer; and the data collection unit is arranged in the thermal-hydrological-mechanical-chemical coupling exploitation experimental device for the deep oil and gas reservoir, and is in communication connection with the computer.

In some embodiments, a volumetric container communicating with the water communicates with the well pattern system through a refrigeration system, and a pressure sensor is connected to each volumetric container; the data collection unit includes the monitoring system and a seepage detection system arranged in the loading bin, the seepage detection system includes a gas-liquid separator, a gas flowmeter, a liquid flowmeter, and a mixed liquid flowmeter; a seepage outflow pipe communicates with the thermal-hydrological-mechanical-chemical coupling exploitation experimental device for the deep oil and gas reservoir, and the gas-liquid separator and the gas flowmeter, the liquid flowmeter and the mixed liquid flowmeter, which are connected in parallel and selectively, are arranged on the seepage outflow pipe in sequence.

Compared with the prior art, the present disclosure has the following technical effects:

The seepage experiment and rock mechanics experiment of a large-scale sample can be carried out in a high-temperature, high-pressure and high-stress in-situ environment, thus achieving the thermal-hydrological-mechanical-chemical coupling process in the large-scale sample under the high-temperature, high-pressure and high-stress in-situ environment.

BRIEF DESCRIPTION OF THE DRAWINGS

To describe the technical solutions of the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

In the drawings: 1, loading bin; 2, sample holding bin; 3, multi-stage arrayed hydraulic cylinder; 4, servo loading pump; 5, bearing column; 6, bearing plate; 7, support seat; 8, sealing block; 9, outer end cover; 10, support plate; 11, telescopic rod; 12, guide column; 13, roller; 14, servo valve; 15, bolt; 16, rock sample; 17, sealing ring.

DETAILED DESCRIPTION OF THE EMBODIMENTS

The following clearly and completely describes the technical solutions in the embodiments of the present disclosure, in conjunction with the accompanying drawings. It is evident that the described embodiments are merely part of the embodiments of the present invention and do not encompass all possible embodiments. All other embodiments that those skilled in the art may derive from the embodiments of the present invention without requiring inventive effort fall within the scope of protection of the present invention.

An objective of the present disclosure is to provide a thermal-hydrological-mechanical-chemical coupling exploitation experimental device for a deep oil and gas reservoir and a simulation system to address the issues present in the existing technology, such that the thermal-hydrological-mechanical coupling experiment of the rock mass can truly reflect the structure characteristics of the rock mass.

In order to make the objectives, features and advantages of the present disclosure more clearly, the present disclosure is further described in detail below with reference to the embodiments.

Embodiment I

Figure 1:
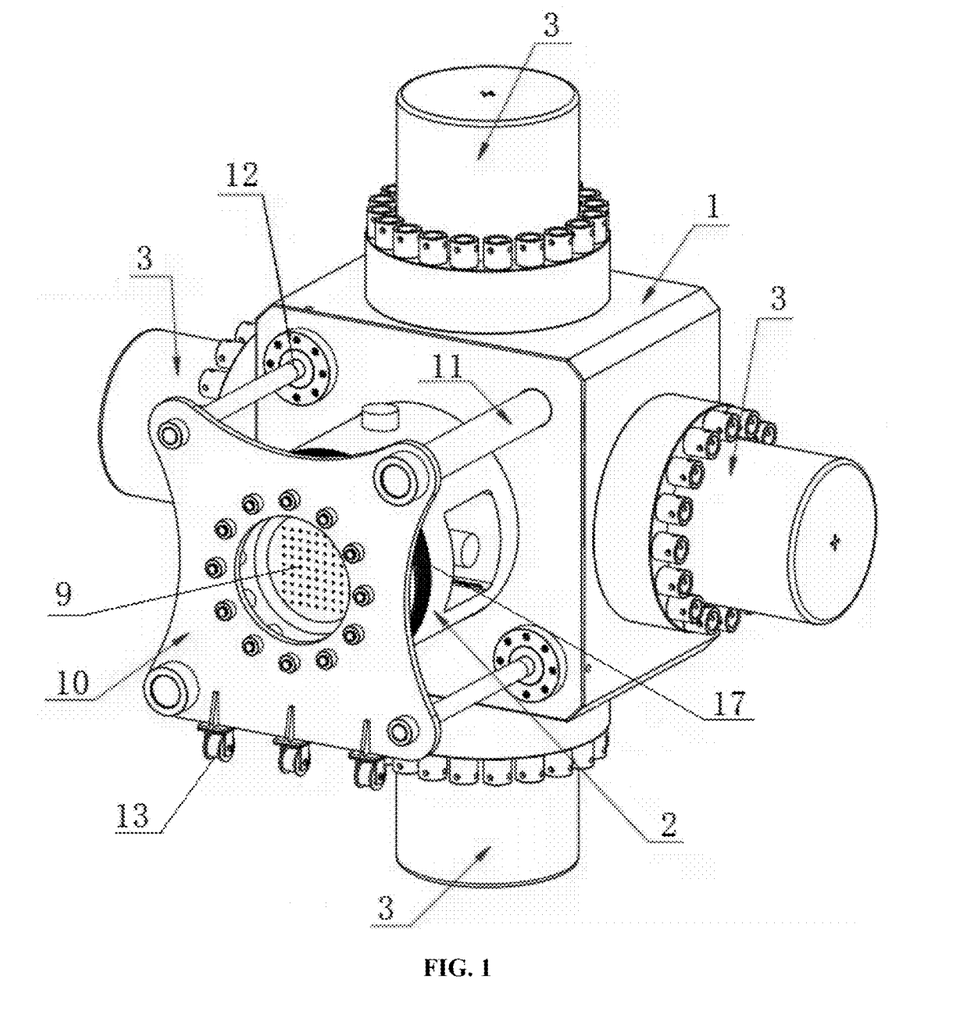
FIG. 1 is a structural schematic diagram of a thermal-hydrological-mechanical-chemical coupling exploitation experimental device for a deep oil and gas reservoir according to an embodiment of the present disclosure.
Figure 2:
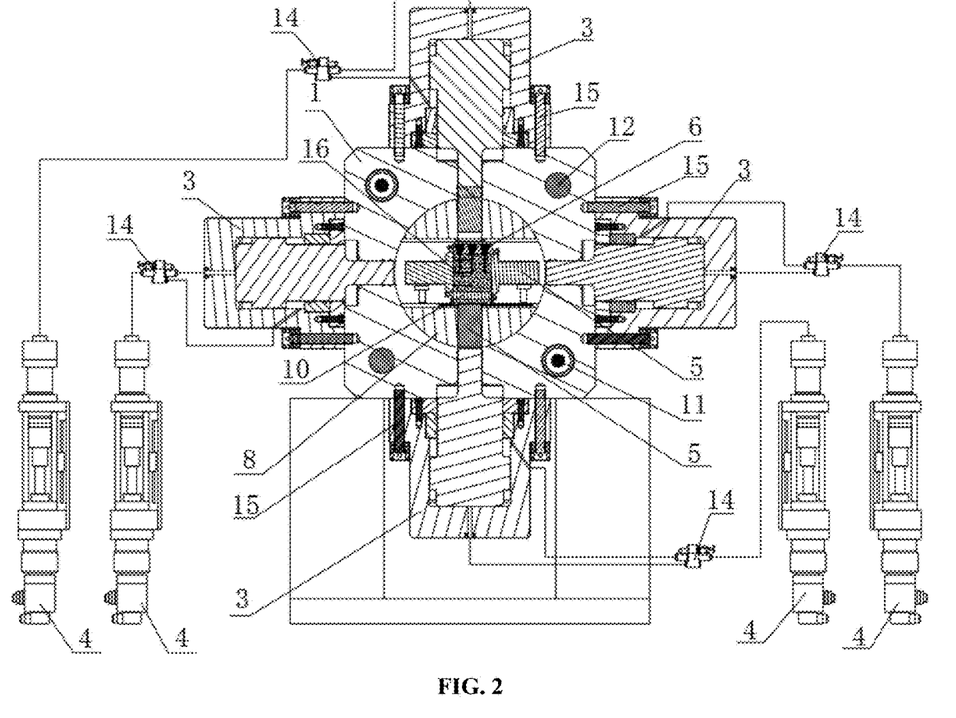
FIG. 2 is a schematic diagram of the internal structure of a thermal-hydrological-mechanical-chemical coupling exploitation experimental device for a deep oil and gas reservoir according to an embodiment of the present disclosure.

As shown in FIG. 1 to FIG. 2, this embodiment provides a thermal-hydrological-mechanical-chemical coupling exploitation experimental device for the deep oil and gas reservoir, including a loading bin 1, a sample holding bin 2, a true triaxial pressure loading mechanism 18, a temperature control system 22, and a monitoring system 23. A sample entry port is formed in one side surface of the loading bin 1, one end of the sample holding bin 2 is slidably arranged in the sample entry port 24, and the other end of the sample holding bin 2 extends out of the side surface of the loading bin 1. The sample holding bin 2 can be sealed and connected with the sample entry port, and is configured for placing and fixing a rock sample 16. Multiple through holes communicating with the sample holding bin 2 are uniformly formed on an outer end cover 9 of the sample holding bin 2, and sealing members 25 are arranged on some of the through holes. The through holes are configured for detecting and adding water, gas, and oil. The true triaxial pressure loading mechanism is arranged on the loading bin 1. The temperature control system is arranged on the true triaxial pressure loading mechanism, and a detection element of the monitoring system is arranged in the rock sample 16 and the sample holding bin 2. The through holes are uniformly formed in the outer end cover 9 of the sample holding bin 2. According to the distribution condition of pores, fractures and holes in the rock sample 16, monitoring points are arranged in the vicinity of pores, fractures and holes for detection, making detection results more accurately reflect the actual situation.

As an alternative scheme, the true triaxial pressure loading mechanism 18 in this embodiment includes an X-axis servo loading system 19, a Y-axis flexible loading system 20, and a Z-axis servo loading system 21. The X-axis servo loading system and the Z-axis servo loading system are symmetrically arranged on respective side surfaces of the loading bin 1. The Y-axis flexible loading system is configured to load confining pressure on the rock sample 16 through the through holes.

Figure 3:
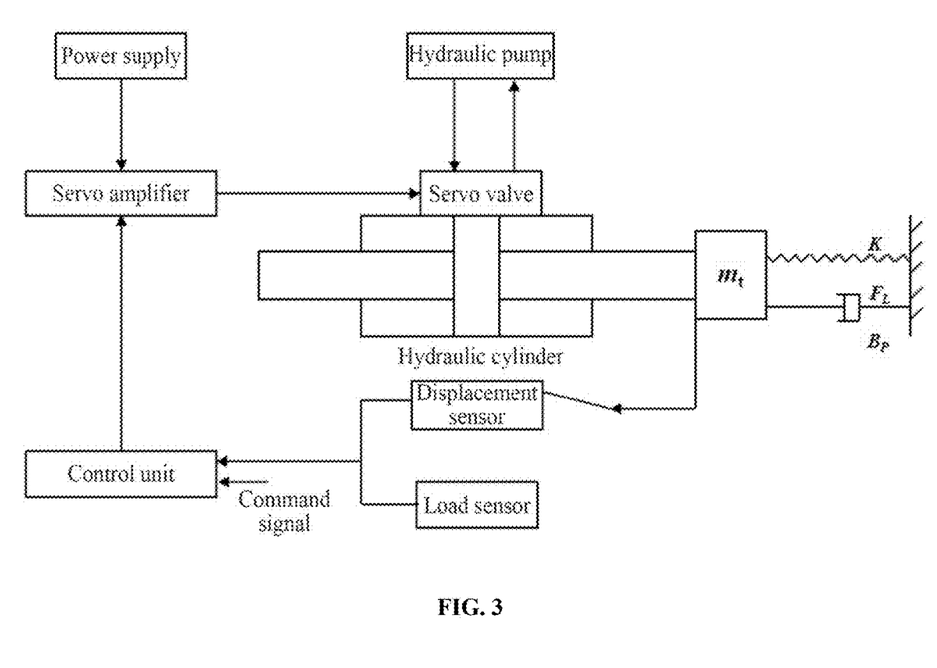
FIG. 3 is a schematic diagram of the operation principle of a multi-stage arrayed hydraulic cylinder according to an embodiment of the present disclosure.

Preferably, each of the X-axis servo loading system and the Z-axis servo loading system in this embodiment is a multi-stage arrayed hydraulic cylinder 3, a servo loading pump 4 is connected to the multi-stage arrayed hydraulic cylinder 3 through a servo valve 4, and a displacement sensor and a load sensor are arranged on the multi-stage arrayed hydraulic cylinder 3. In this embodiment, the multi-stage arrayed cylinder technology employs a loading system of a high-precision servo loading pump 4, and two sets of loading systems, i.e., a low-pressure high-speed loading system and a high-pressure low-speed loading system, are provided to achieve accurate loading and control of the composite high stress, as illustrated in FIG. 3.

As an alternative embodiment, in this embodiment, multiple sealing blocks 8 are fixedly arranged at the top and bottom of the sample holding bin 2, an insertion hole is formed in each sealing block 8, a bearing column 5 is slidably arranged in the insertion hole, a bearing plate 6 is connected to an upper bearing column 5, and a support seat 7 is connected to a lower bearing column 5 and is configured for fixing the rock sample 16. T-shaped bearing columns 5 are configured to be arranged on both sides of the rock sample 16, and the bearing columns 5 are used to be connected to the X-axis servo loading system and the Z-axis servo loading system, thus making the X-axis and the Z-axis apply rigid pressure directly.

As an alternative scheme, in this embodiment, the temperature control system 22 is arranged on the Y-axis flexible loading system, and includes a temperature sensor 26, a heating system 27, and a refrigeration system 28. The heating system and the refrigeration system are arranged on a circulation pipeline of the Y-axis flexible loading system. Alternatively, the refrigeration system is arranged on a pipeline for injecting water into the rock sample 16 or the sample holding bin 2. In this embodiment, rigid loading on two directions by the X-axis and Z-axis loading cylinders and flexible loading (Y axis) in one direction are adopted, and meanwhile, precise servo control is adopted, which reduces the end-face friction effect, and achieves the precise control under high pressure and high stress. In the high-stress, high-temperature and high-pressure environment, a saturation method of measuring resistance and a dynamic monitoring technology of temperature field and pressure field are used to achieve high restoration of the in-situ environment of the formation. The heating system preferably employs an electromagnetic heating mode for heating a confining pressure liquid to simulate the high-temperature condition. The refrigeration system is preferably an air-conditioning refrigeration system for cooling the water entering the sample holding bin 2, thus preventing high heat of the confining pressure liquid from damaging the equipment.

As an alternative scheme, the monitoring system in this embodiment includes an acoustic emission sensor, a pressure sensor and a temperature sensor, which are arranged in the loading bin 1, and a resistive probe configured to be arranged in the rock sample 16. In this embodiment, rock fracture information monitoring and mechanism analysis are carried out based on acoustic emission monitoring technology (AE). Akaike information criterion (AIC) algorithm is used to pick up an acoustic emission signal, a downhill simplex positioning algorithm is used for locating seismic source, and a hybrid moment tensor inversion method is used to analyze the fracture mechanism of the seismic source in different fracturing stages. The pressure sensor and the temperature sensor are used to detect the pressure and temperature of the confining pressure liquid. The resistive probe can convert the resistance into a saturation parameter by a computer operation system.

As an alternative scheme, an outer end of the sample holding bin 2 in this embodiment is provided with a sealing ring 17 for sealing the sample entry port, and the sealing element is a ferrule-type joint. The rock sample 16 is sealed with a heat shrinkable tube, and the heat shrinkable tube is made of tetrafluoroethylene resin. In this embodiment, the ferrule-type joint is designed to resist high temperature and high pressure, which can seal a borehole under high temperature and high pressure. The heat shrinkable tube is improved in material and process, and is improved with tetrafluoroethylene resin, of which the shrinkage temperature is higher than 180° C., the shrinkage ratio is 1.8:1, and the service temperature is −55° C.-260° C. The sealing ring 17 is an indenter sealing gasket made of silicon rubber to achieve the sealing of a seepage cavity under high-temperature and high-pressure conditions.

As an alternative scheme, in this embodiment, a support plate 10 is connected to the outer end cover 9 of the sample holding bin 2 by a bolt 15, a pair of telescopic rods 11 and a pair of guide columns 12 are arranged on four corners of the support plate 10, respectively, and the telescopic rods 11 and the guide columns 12 each are arranged diagonally. Multiple rollers 13 are arranged at the bottom of the support plate 10, and the rollers 13 are used for rolling on a support platform. The telescopic rod 11 is preferably a hydraulic cylinder.

In this embodiment, the thermal-hydrological-mechanical-chemical coupling exploitation experimental device for the deep oil and gas reservoir is integrated by components with different functions, which can reduce the real formation stress, formation pressure and formation temperature, and can perform mechanical experiments, hydraulic fracturing and flow testing, and thermal-hydrological-mechanical coupling characteristic behaviors on the rock sample 16, so as to achieve well pattern development modes of different types, simulate various exploitation methods and development modes, and specifically achieve the reduction of high-temperature, high-pressure (250° C., 200 MPa) and high-stress in-situ environment. Under the condition of high temperature, high pressure and high stress, both seepage experiment and rock mechanics experiment can be carried out to achieve the effective combination. On the basis of high temperature, high pressure and high stress, a large-scale rock sample (300×300×300 mm$^3$) can be placed into the loading bin 1 for rock mechanics and seepage mechanics experiments. The well pattern system is arranged through cable through holes in the outer end cover 9 in FIG. 1, and the changes of saturation, pressure and temperature in the rock sample 16 can be dynamically monitored through the monitoring system.

Embodiment II

Figure 4:
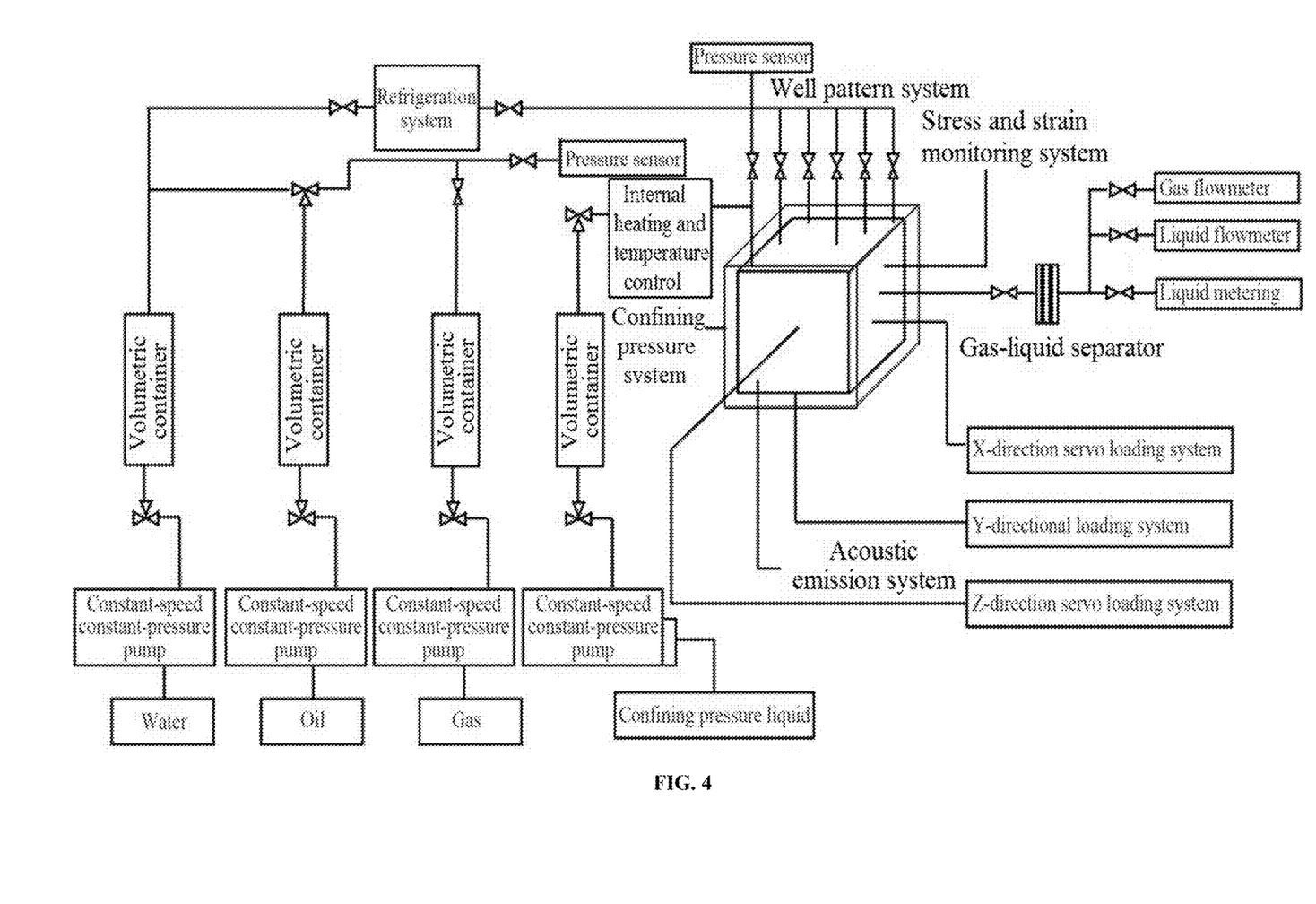
FIG. 4 is a schematic diagram of the experimental principle of a thermal-hydrological-mechanical-chemical coupling exploitation experimental device for a deep oil and gas reservoir according to an embodiment of the present disclosure.

As shown in FIG. 3 to FIG. 4, a thermal-hydrological-mechanical-chemical coupling simulation system for the deep oil and gas reservoir includes the thermal-hydrological-mechanical-chemical coupling exploitation experimental device for the deep oil and gas reservoir above, a seepage system, and a data collection and analysis system. The seepage system includes constant-speed and constant-pressure pumps, volumetric containers, and a well pattern system. The well pattern system is configured to be arranged on a rock sample 16 in the thermal-hydrological-mechanical-chemical coupling exploitation experimental device for the deep oil and gas reservoir. Water, gas and oil are connected to the respective volumetric containers through the respective constant-speed and constant-pressure pumps. The volumetric containers communicate with the well pattern system. The thermal-hydrological-mechanical-chemical coupling exploitation experimental device for the deep oil and gas reservoir can carry out two-rigid and one-flexible type triaxial pressure loading on the rock sample 16. The data collection and analysis system includes a data collection unit and a computer. The data collection unit is arranged in the thermal-hydrological-mechanical-chemical coupling exploitation experimental device for the deep oil and gas reservoir, and the data collection unit is in communication connection with the computer.

As an alternative scheme, in this embodiment, the volumetric container communicating with the water communicates with the well pattern system through a refrigeration system, and a pressure sensor is connected to each volumetric container. The data collection unit includes a monitoring system and a seepage detection system arranged in the loading bin 1. The seepage detection system includes a gas-liquid separator, a gas flowmeter, a liquid flowmeter, and a mixed liquid flowmeter. The seepage outflow pipe communicates with the thermal-hydrological-mechanical coupling exploitation experimental device of a deep oil and gas reservoir. The gas-liquid separator and the gas flowmeter, the liquid flowmeter and the mixed liquid flowmeter which are connected in parallel and selectively are arranged on the seepage outflow pipe in sequence.

In this embodiment, a thermal-hydrological-mechanical-chemical coupling simulation system for the deep oil and gas reservoir takes a water-driven gas seepage experiment under the condition of high temperature and high pressure as an example, and the specific implementation steps are as follows.

S1. According to the actual geological outcrop data, a large-scale rock sample 16 is prepared, and positions of a production well and bottom water are determined according to the actual geological section map of an oil reservoir; According to actual geological conditions, the pressure, saturation and temperature measuring points of the rock sample 16 are designed, and then the point arrangement is arranged, and then the rock sample 16 is encapsulated using a heat shrinkable tube.

S2. The encapsulated rock sample 16 is placed into the sample holding bin 2 of the loading bin 1, and various loading columns are connected and assembled, the rock sample slides into the sample holding bin 2 to enter the loading bin 1, and the rock sample 16 in the loading bin 1 is vacuumized by a high-pressure pump. When the pressure sensor in the rock sample 16 shows that the pressure tends to be stable, it is determined that the rock sample 16 is completely saturated with gas, and can simulate gas reservoir conditions.

S3. The pressure in the loading bin 1 is loaded and pressurized by the multi-stage arrayed hydraulic cylinders 3, and confining pressure liquid is heated by the heating system in the temperature control system first, such that the temperature can be increased in a gradient of 5° C. till to reach the formation temperature. The confining pressure liquid is injected into a high-temperature and high-pressure bin by a constant-speed and constant-pressure pump at a constant pressure of 5 MPa, and then the gas is injected into the rock sample 16 by a constant-speed and constant-pressure pump at a constant pressure of 1 MPa. After the gas is injected for a period of time, when the flow rate of the gas at an outlet end is found to be stable through the gas flowmeter, a valve at the outlet end is closed to keep the confining pressure higher than the gas injection pressure by 5 MPa. The confining pressure and gas injection pressure are continuously increased until the pressure sensor of the confining pressure shows that the confining pressure reaches the original formation pressure, a pressure probe shows that the pore pressure in the rock sample 16 is consistent with the gas injection pressure, and the temperature sensor shows that the temperature reaches the original formation temperature; and then the constant-speed and constant-pressure pumps and valves for the confining pressure liquid and the gas injection are closed. Then, the constant-speed and constant-pressure pump for water injection is turned on until the pressure sensor shows that the water injection pressure is consistent with the gas injection pressure. Afterwards, the valve is opened to simulate a water-driven gas seepage experiment, and meanwhile, the valve at the outlet end is opened, and the saturation, pressure and temperature changes in the rock sample 16 are observed through the saturation, pressure and temperature measuring points on the monitoring system. Through various arranged monitoring points, the pressure inside the rock sample 16 and the change of water saturation in the fracture can be monitored, and the gas production and water production can be recorded and measured by a flowmeter. The gas production rate is changed, and then the fluid migration law and residual gas distribution characteristics under different gas production rates and different fracture development modes are observed.

S4. The gas production and water production flow at the outlet end are recorded by the liquid flowmeter and the gas flowmeter at the outlet end, and the water production at the outlet is recorded by a liquid volume metering device. When the gas flowmeter shows that the gas production rate at the outlet is zero, or until the gas production rate approaches zero, the constant-speed and constant-pressure pump for injecting water is turned off, the constant-speed and constant-pressure pump for injecting water is turned off, and the corresponding valve is closed. Afterwards, the refrigeration system is turned on to cool the water entering the sample holding bin 2, thus reducing the temperature in the rock sample 16 until the temperature in the rock sample 16 is normal temperature. At this time, the confining pressure liquid is returned, the pipeline is dismounted, the data is recorded, and the experiment is stopped.

Specific examples are used herein for illustration of the principles and embodiments of the present disclosure. The description of the embodiments is merely used to help illustrate the method and its core principles of the present disclosure. In addition, those of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. A thermal-hydrological-mechanical-chemical coupling exploitation experimental device for a deep oil and gas reservoir, comprising a loading bin, a sample holding bin, a true triaxial pressure loading mechanism, a temperature control system, and a monitoring system, wherein a sample entry port is formed in one side surface of the loading bin, the sample holding bin has one end slidably arranged in the sample entry port and another end extending out of the side surface of the loading bin; the sample holding bin is able to be sealed and connected with the sample entry port, and is configured for placing and fixing a rock sample; a plurality of through holes communicating with the sample holding bin are uniformly formed on an outer end cover of the sample holding bin, and sealing members are respectively arranged at the plurality of through holes; the plurality of through holes are configured for pipelines containing water, gas and oil and cables for detecting the water, the gas and the oil to pass through; the true triaxial pressure loading mechanism is arranged on the loading bin; the temperature control system is arranged on the true triaxial pressure loading mechanism, and detection elements of the monitoring system are arranged in the rock sample and the sample holding bin;

wherein the true triaxial pressure loading mechanism comprises an X-axis servo loading system, a Y-axis flexible loading system, and a Z-axis servo loading system; the X-axis servo loading system and the Z-axis servo loading system are symmetrically arranged on respective side surfaces of the loading bin; and the Y-axis flexible loading system is arranged to be in communication with the through holds on the outer end of the sample holding bin and is configured to load confining pressure on the rock sample through the plurality of through holes;

wherein the temperature control system is arranged on the Y-axis flexible loading system, and comprises a temperature sensor, a heating system, and a refrigeration system; and the heating system and the refrigeration system are arranged on a circulation pipeline of the Y-axis flexible loading system; wherein each of the X-axis servo loading system and the Z-axis servo loading system is a multi-stage arrayed hydraulic cylinder, a servo loading pump connected to the multi-stage arrayed hydraulic cylinder, and a displacement sensor and a load sensor are arranged on the multi-stage arrayed hydraulic cylinder.

2. The thermal-hydrological-mechanical-chemical coupling exploitation experimental device for the deep oil and gas reservoir according to claim 1, wherein a plurality of sealing blocks are fixedly arranged at a top and a bottom of the sample holding bin, an insertion hole is formed in each sealing block, a bearing column is slidably arranged in the insertion hole, a bearing plate is connected to an upper bearing column, and a support seat is connected to a lower bearing column and is configured for fixing the rock sample; T-shaped bearing columns are configured to be arranged on both sides of the rock sample, and the bearing columns are used to connect with the X-axis servo loading system and the Z-axis servo loading system.

3. The thermal-hydrological-mechanical-chemical coupling exploitation experimental device for the deep oil and gas reservoir according to claim 1, wherein the detection elements of the monitoring system comprise an acoustic emission sensor, a pressure sensor, a temperature sensor, which are arranged in the loading bin, and a resistive probe configured to be arranged in the rock sample.

4. The thermal-hydrological-mechanical-chemical coupling exploitation experimental device for the deep oil and gas reservoir according to claim 1, wherein an outer end of the sample holding bin is provided with a sealing ring for sealing the sample entry port, and the sealing member is a ferrule-type joint; and a heat shrinkable tube is configured for sealing the rock sample and is made of tetrafluoroethylene resin.

5. The thermal-hydrological-mechanical-chemical coupling exploitation experimental device for the deep oil and gas reservoir according to claim 1, wherein a support plate is connected to the outer end cover of the sample holding bin by a bolt, a pair of telescopic rods and a pair of guide columns are arranged on four corners of the support plate respectively, the telescopic rods and the guide columns each are arranged diagonally, and a plurality of rollers are arranged on a bottom of the support plate and are configured for rolling on a support platform.

6. A thermal-hydrological-mechanical-chemical coupling simulation system for a deep oil and gas reservoir, comprising the thermal-hydrological-mechanical-chemical coupling exploitation experimental device for the deep oil and gas reservoir according to claim 1, a seepage system, and a data collection and analysis system, wherein the seepage system comprises constant-speed and constant-pressure pumps, volumetric containers, and a well pattern system; the well pattern system is configured to be arranged on the rock sample in the thermal-hydrological-mechanical-chemical coupling exploitation experimental device for the deep oil and gas reservoir; water, gas and oil are connected to respective volumetric containers through respective constant-speed and constant-pressure pumps; the volumetric containers communicate with the well pattern system; and the thermal-hydrological-mechanical-chemical coupling exploitation experimental device for the deep oil and gas reservoir is able to carry out two-rigid and one-flexible type triaxial pressure loading on the rock sample; the data collection and analysis system comprises a data collection unit and a computer; and the data collection unit is arranged in the thermal-hydrological-mechanical-chemical coupling exploitation experimental device for the deep oil and gas reservoir, and is in communication connection with the computer.

7. The thermal-hydrological-mechanical-chemical coupling simulation system for the deep oil and gas reservoir according to claim 6, wherein a volumetric container communicating with the water communicates with the well pattern system through a refrigeration system, and a pressure sensor is connected to each volumetric container; the data collection unit comprises the monitoring system and a seepage detection system arranged in the loading bin, the seepage detection system comprises a gas-liquid separator, a gas flowmeter, a liquid flowmeter, and a mixed liquid flowmeter; a seepage outflow pipe communicates with the thermal-hydrological-mechanical-chemical coupling exploitation experimental device for the deep oil and gas reservoir, and the gas-liquid separator and the gas flowmeter, the liquid flowmeter and the mixed liquid flowmeter, which are connected in parallel and selectively, are arranged on the seepage outflow pipe in sequence.

8. The thermal-hydrological-mechanical-chemical coupling simulation system for the deep oil and gas reservoir according to claim 6, wherein each of the X-axis servo loading system and the Z-axis servo loading system is a multi-stage arrayed hydraulic cylinder, a servo loading pump is connected to the multi-stage arrayed hydraulic cylinder, and a displacement sensor and a load sensor are arranged on the multi-stage arrayed hydraulic cylinder.

9. The thermal-hydrological-mechanical-chemical coupling simulation system for the deep oil and gas reservoir according to claim 6, wherein a plurality of sealing blocks are fixedly arranged at a top and a bottom of the sample holding bin, an insertion hole is formed in each sealing block, a bearing column is slidably arranged in the insertion hole, a bearing plate is connected to an upper bearing column, and a support seat is connected to a lower bearing column and is configured for fixing the rock sample; T-shaped bearing columns are configured to be arranged on both sides of the rock sample, and the bearing columns are used to connect with the X-axis servo loading system and the Z-axis servo loading system.

10. The thermal-hydrological-mechanical-chemical coupling simulation system for the deep oil and gas reservoir according to claim 6, wherein the monitoring system comprises an acoustic emission sensor, a pressure sensor, a temperature sensor, which are arranged in the loading bin, and a resistive probe configured to be arranged in the rock sample.

11. The thermal-hydrological-mechanical-chemical coupling simulation system for the deep oil and gas reservoir according to claim 6, wherein an outer end of the sample holding bin is provided with a sealing ring for sealing the sample entry port, and the sealing member is a ferrule-type joint; and a heat shrinkable tube is configured for sealing the rock sample and is made of tetrafluoroethylene resin.

12. The thermal-hydrological-mechanical-chemical coupling simulation system for the deep oil and gas reservoir according to claim 6, wherein a support plate is connected to the outer end cover of the sample holding bin by a bolt, a pair of telescopic rods and a pair of guide columns are arranged on four corners of the support plate respectively, the telescopic rods and the guide columns each are arranged diagonally, and a plurality of rollers are arranged on a bottom of the support plate and are configured for rolling on a support platform.

* * * * *